United States Patent
Li et al.

(10) Patent No.: US 10,123,748 B2
(45) Date of Patent: Nov. 13, 2018

(54) ACTIVE PATIENT RISK PREDICTION

(71) Applicant: International Business Machines Corporation, Armonk, NY (US)

(72) Inventors: Hongfei Li, Briarcliff Manor, NY (US); Buyue Qian, Ossining, NY (US); Fei Wang, Briarcliff, NY (US); Xiang Wang, Santa Clara, CA (US)

(73) Assignee: International Business Machines Corporation, Armonk, NY (US)

( * ) Notice: Subject to any disclaimer, the term of this patent is extended or adjusted under 35 U.S.C. 154(b) by 964 days.

(21) Appl. No.: 14/527,824

(22) Filed: Oct. 30, 2014

(65) Prior Publication Data
US 2016/0120481 A1 May 5, 2016

(51) Int. Cl.
*G16H 50/00* (2018.01)
*A61B 5/00* (2006.01)
*G16H 50/30* (2018.01)
*G16H 50/70* (2018.01)
*G06F 19/00* (2018.01)
*A61B 5/055* (2006.01)
(Continued)

(52) U.S. Cl.
CPC .......... *A61B 5/7275* (2013.01); *G06F 19/00* (2013.01); *G16H 50/30* (2018.01); *G16H 50/70* (2018.01); *A61B 5/055* (2013.01)

(58) Field of Classification Search
CPC ........ G06Q 50/22; G06Q 50/24; G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00;
(Continued)

(56) References Cited

U.S. PATENT DOCUMENTS

2008/0235052 A1 9/2008 Node-Langlois et al.
2012/0089551 A1 4/2012 Ebadollahi et al.
(Continued)

FOREIGN PATENT DOCUMENTS

WO    WO-2010044683 A1 * 4/2010 ............. G06F 19/24

OTHER PUBLICATIONS

Settles, Burr; "Active Learning Synthesis Lectures on Artificial Intelligence and Machine Learning"; Morgan & Claypool Publishers; Published: Jun. 2012; Printed: Aug. 11, 2014; <http://www.morganclaypool.com/doi/abs/10.2200/S00429ED1V01Y>.

(Continued)

*Primary Examiner* — Joseph D Burgess
(74) *Attorney, Agent, or Firm* — Minh-Hien Vo

(57) ABSTRACT

Electronic health records of a plurality of patients are received. A risk prediction model for a disease based on the electronic health records of the plurality of patients is created. An electronic health record of an original patient is received. A neighboring group of patients of the plurality of patients is identified, wherein the neighboring group of patients is two or more patients similar to the original patient. An ordering of the two or more patients of the neighboring group of patients is received, wherein the ordering of the two or more patients of the neighboring group of patients is based upon how similar each patient of the two or more patients is to the original patient. The risk prediction model is updated based on the ordering of the two or more patients of the neighboring group of patients.

20 Claims, 3 Drawing Sheets

(58) Field of Classification Search
CPC ........ G16H 40/00; G16H 40/20; G16H 40/40;
G16H 40/60; G16H 40/63; G16H 40/67;
G16H 50/00; G16H 70/00; G16H 70/20;
G16H 70/40; G16H 70/60; G16H 80/00
See application file for complete search history.

(56) References Cited

U.S. PATENT DOCUMENTS

| | | | |
|---|---|---|---|
| 2012/0166208 A1* | 6/2012 | Gillam | G06Q 50/22 |
| | | | 705/2 |
| 2013/0311193 A1 | 11/2013 | Know et al. | |
| 2014/0052474 A1* | 2/2014 | Madan | G06F 19/3437 |
| | | | 705/3 |
| 2014/0058986 A1 | 2/2014 | Boss et al. | |

OTHER PUBLICATIONS

Wang, Fei, et al.; "iMet: Interactive Metric Learning in Healthcare Applications"; IBM TJ Watson Research Center; pp. 944-954; Copyright SIAM.

Zhou, Xiang Sean, et al.; "Relevance feedback in image retrieval: A comprehensive review"- Multimedia Systems 8; pp. 536-544; 2003; Multimedia Systems Copyright Springer-Verlag 2003.

\* cited by examiner

ACTIVE PATIENT RISK PREDICTION

BACKGROUND OF THE INVENTION

The present invention relates generally to the field of active learning, and more particularly to predicting the risk of patients to certain diseases using electronic health records (EHR) along with active learning with relative similarities.

Active learning has been extensively studied and successfully applied to solve real world problems. The typical setting of active learning methods is to query absolute questions. The key idea of active learning is that a machine learning algorithm can achieve higher accuracy with fewer training labels if it is allowed to choose the data from which it learns. Active learning extends machine learning by allowing learning algorithms to typically query the labels from an oracle (e.g., a human annotator) that already understands the problem for currently unlabeled instances. Though enormous progress has been made in the active learning field in recent years, traditional active learning assumes that the questions prompted by a machine can be confidently answered by human experts, which may not be the case in many real world applications.

In a medical application where the goal is to predict the risk of patients on certain diseases using EHR, the absolute questions may take the form of, "Will this patient suffer from Alzheimer's later in his/her life?" or, "Are these two patients similar or not?" Due to the excessive requirements of domain knowledge, such absolute questions are usually difficult to answer, even for experienced medical experts. In addition, the performance of absolute question focused active learning methods is less stable, since incorrect answers often occur which can be detrimental to the risk of the prediction model.

SUMMARY

Embodiments of the present invention include a method, computer program product, and system for updating a patient risk prediction model. In one embodiment, electronic health records of a plurality of patients are received. A risk prediction model for a disease based on the electronic health records of the plurality of patients is created. An electronic health record of an original patient is received. A neighboring group of patients of the plurality of patients is identified, wherein the neighboring group of patients is two or more patients similar to the original patient. An ordering of the two or more patients of the neighboring group of patients is received, wherein the ordering of the two or more patients of the neighboring group of patients is based upon how similar each patient of the two or more patients is to the original patient. The risk prediction model is updated based on the ordering of the two or more patients of the neighboring group of patients.

DETAILED DESCRIPTION

Figure 1:
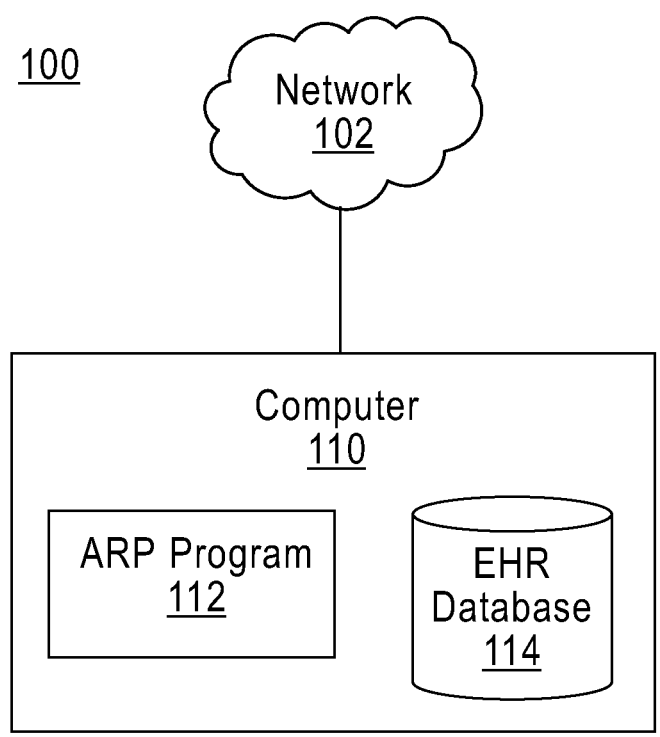
FIG. 1 is a functional block diagram of a data processing environment, in accordance with an embodiment of the present invention.

Embodiments of the present invention allow for the updating of a patient risk prediction model. The active patient risk prediction (ARP) program receives electronic health records for an original patient, the subject of the risk prediction, and a group of patients from which to create the risk prediction model. The ARP program creates the risk prediction model from the group of patients and then identifies a smaller (neighboring) group of patients from the group of patients that is similar to the original patient. An expert orders the group of patients and the original patient based upon their similarities. The ARP program receives this ordering and updates the risk prediction model. Determining neighboring groups of patients, ordering them, and then updating the risk prediction model based upon the ordering can happen any number of times and the goal is to create an accurate risk prediction model. ARP program then predicts the risk of the original patient suffering a disease, or diseases, based upon the risk prediction model.

Some embodiments of the present invention recognize that active patient risk prediction (ARP), is a way to explore easier active learning for medical data, so as to address the dilemma when medical experts cannot confidently provide absolute labels for patients. Asking easier questions can effectively reduce the time and cost when applying active learning techniques to real world problems. A key step to active patient risk prediction is to select informative queries, by answering which prediction model is improved maximally. The present invention, rather than asking for absolute questions such as labels, asks humans to place an ordering (possibly partial ordering) on the relative similarity of the neighbors to the instance that they are neighbors of.

Specifically, a computer prompts a patient along with the patients who are similar to him/her (nearest neighbors), and then a medical expert is asked to sort or partially sort (from the most similar one to the lease similar one) the neighboring patients according to the relative similarity to the patient that they are neighbors of. Since the active learning scheme is performed on neighbor sets rather than instances, the focus is on selecting the most informative neighbor sets which is cased as a counting set cover problem. Counting set cover is an efficient combinational algorithm to perform entity ranking/selection, and by using, the aim is to locate the instance whose neighborhood is most influential to the graph structure. This query scheme selects the most informative neighborhood to query, and the advice of the human experts are enforced as constraints in the subsequent updating of the neighborhood structure, which is later used to help better propagate labels on the graph with the process being repeated.

The main advantage of querying neighborhood structure/weights is that the relative questions are easier to answer for medical experts. This is particularly useful to active learning in many specialized domains, such as the medical field, where the absolute questions are difficult to answer even for people with proficient domain knowledge. Additionally, the benefits of using a counting set cover algorithm to estimate the importance of a patient neighborhood include: (i) neighbor sets that are essential to maintain the graph structure can be naturally found through solving a set cover problem; and (ii) counting with different weighting schemes would emphasize different notions of the importance of graph structure, which enriches the flexibility of active neighborhood selection.

The present invention will now be described in detail with reference to the Figures. FIG. 1 is a functional block diagram illustrating a data processing environment, generally designated 100, in accordance with one embodiment of the present invention. FIG. 1 provides only an illustration of one implementation and does not imply any limitations with regard to the systems and environments in which different embodiments may be implemented. Many modifications to the depicted embodiment may be made by those skilled in the art without departing from the scope of the invention as recited by the claims.

An embodiment of data processing environment 100 includes computer 110, interconnected over network 102. Network 102 can be, for example, a local area network (LAN), a telecommunications network, a wide area network (WAN) such as the Internet, or any combination of the three, and include wired, wireless, or fiber optic connections. In general, network 102 can be any combination of connections and protocols that will support communications between computer 110 and any other computer connected to network 102, in accordance with embodiments of the present invention.

In example embodiments, computer 110 may be a laptop, tablet, or netbook personal computer (PC), a desktop computer, a personal digital assistant (PDA), a smart phone, or any programmable electronic device capable of communicating with any computing device within data processing environment 100. In certain embodiments, computer 110 collectively represents a computer system utilizing clustered computers and components (e.g., database server computers, application server computers, etc.) that act as a single pool of seamless resources when accessed by elements of data processing environment 100, such as in a cloud computing environment. In general, computer 110 is representative of any electronic device or combination of electronic devices capable of executing computer readable program instructions. Computer 110 may include components as depicted and described in further detail with respect to FIG. 3, in accordance with embodiments of the present invention.

Computer 110 includes active patient risk program (ARP) program 112 and electronic health record (EHR) database 114. ARP program 112 is a program, application, or subprogram of a larger program that creates a risk prediction model for a disease using EHRs. ARP program 112 then determines a neighboring group of patients to the original patient using the risk prediction model and medical experts rank the neighboring group of patients and the original patient. ARP program 112 then updates the risk prediction model using the rankings, and estimates risk that a patient will suffer from a certain disease. EHR database 114 contains medical information about individual patients. An EHR is a record in digital format that is theoretically capable of being shared across different health care settings and may include a wide range of data, including, but not limited to, demographics, medical history, medication and allergies, immunization status, laboratory test results, radiology images, vital signs, and personal statistics like age and weight.

ARP program 112 receives EHRs about multiple patients including the subject patient that will have their risk estimated for a certain disease. ARP program 112 creates a risk prediction model from the EHRs of the multiple patients. ARP program 112 identifies a neighboring group of patients, from the multiple patients, that the subject patient is close in risk for the disease based on the risk prediction model and notifies medical experts of the determined neighboring group of patients. ARP program 112 receives an ordering of the neighboring group of patients and the subject patient from the medical experts based on the risk of the disease. ARP program 112 updates the risk prediction model based on the ordering of the neighboring group of patients and the subject patients based on the risk of the disease. ARP program 112 determines if the risk prediction model is accurate. If the risk prediction model is not accurate enough, then ARP program 112 returns to identifying a neighboring group of patients to the subject patient based on the risk of the disease. If the risk prediction model is accurate enough, ARP program 112 estimates the risk of the subject patient.

The risk prediction model created by ARP program 112 contains a number of variables that will now be defined. There are a set of $\eta$ patients $\mathcal{P} = \{p_1, p_2, p_3 \ldots, p_n\}$, and each patient is defined as a classification problem on a set of m possible diseases (labels). The $\eta$ patients were examined periodically, and were labeled since it is known what diseases they eventually suffer from. A binary matrix B ($B \in R^{n \times m}$) carry the given labels (diseases), where $b_{ij}=1$ if patient $p_i$ suffers from disease j, and $b_{ij}=0$ otherwise. Here, $\mathcal{G}_{pi}$ denotes a group of patients (neighbor set) which consists of the patients that are similar (nearest neighbors) to patient $p_i$. For different patients the size of the neighbor set may differ. A graph of the patients is constructed, which is fully defined by a patient similarity matrix S (sparse), where an entry $S_{ij}=1$ if patient i and j are exactly the same, and $S_{ij}=0$ if patient i and j are not similar. The relative similarity provided by medical experts are enforced to the learning of the patient similarity matrix S, such that better patient similarity is learned from human feedback, which in turn produces a better estimate of patient risks. $S_{ij} \neq S_{ji}$ is possible and allowed. The row or column vectors are often referred to as matrices, for instance, i-th row and j-th column vectors of the matrix S are denoted as $S_i$· and $S_j$·, respectively. The risk prediction model created by ARP program 112 iterates between the learning of the patient similarity matrix S—updating a row of S in each iteration based on the relative similarities provide by medical experts, and the query selection—identify the most informative group of neighboring patients by ordering.

A user interface (not shown) is a program that provides an interface between a user and ARP program 112. Any or all of the steps performed by ARP program 112 can be facilitated by the user interface on computer 110 or any other computer connected to computer 110 via network 102. A user interface refers to the information (such as graphic, text, and sound) a program present to a user and the control sequences the user employs to control the program. There are many types of user interfaces. In one embodiment, the user interface may be a graphical user interface (GUI). A GUI is a type of user interface that allows users to interact with electronic devices, such as a keyboard and mouse, through graphical icons and visual indicators, such as secondary notations, as opposed to text-based interfaces, typed command labels, or text navigation. In computers, GUIs were introduced in reaction to the perceived steep learning curve of command-line interfaces, which required commands to be typed on the keyboard. The actions in GUIs are often performed through direct manipulation of the graphics elements.

EHR database 114 resides on computer 110. In another embodiment, EHR database 114 may reside on another device or computer within data processing environment 100 or any other device not within data processing environment 100, accessible via network 102. A database is an organized collection of data. Data found in a database is typically organized to model relevant aspects of reality in a way that supports processes requiring the information found in the database. EHR database 114 can be implemented with any type of storage device capable of storing data that may be accessed and utilized by computer 110, such as a database server, a hard disk drive, or a flash memory. In other embodiments, EHR database can represent multiple storage devices within computer 110.

Alternatively, EHR database 114 can be any computer readable storage medium as found in the art. For example, the computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing.

EHR database 114 may include medical information about individual patients. An EHR is a record in digital format that is theoretically capable of being shared across different health care settings and may include a wide range of data, including, but not limited to, demographics, medical history, medication and allergies, immunization status, laboratory test results, radiology images, vital signs, and personal statistics like age and weight. The EHR database 114 is designed to represent data that accurately captures the state of the patient at all times. It allows for an entire patient history to be viewed without the need to track down the patient's previous medical record volume and assists in ensuring data is accurate, appropriate, and legible.

Figure 2:
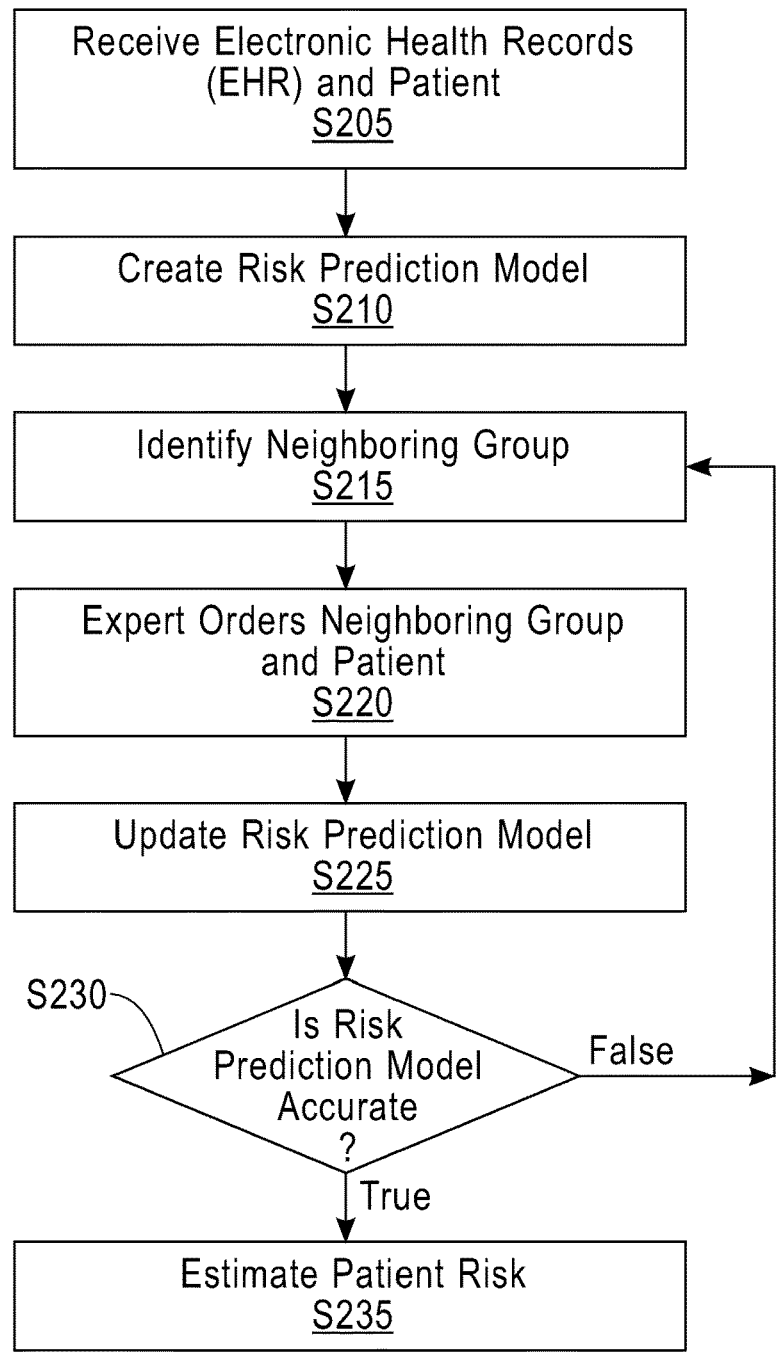
FIG. 2 is a flowchart depicting operational steps of a program for active patient risk prediction, in accordance with an embodiment of the present invention.

FIG. 2 is a flowchart of workflow 200 depicting operational steps for active patient risk prediction, in accordance with an embodiment of the present invention. In one embodiment, the steps of the workflow are performed by ARP program 112. Alternatively, steps of the workflow can be performed by any other program while working with ARP program 112. In a preferred embodiment, a user, via a user interface discussed previously, can invoke workflow 200 upon determining that they would like predict a patient's risk. In an alternative embodiment, workflow 200 can be invoked automatically under the control of another program, for example, upon the user entering data about a subject patient in the EHR record database 114 and that update being sent to ARP program 112 to begin a step in workflow 200.

ARP program 112 receives electronic health records (EHR) about multiple patients and in addition EHR about the subject patient (step S205). In an embodiment, ARP program 112 may receive the information about the multiple patients and the subject patient information from a medical expert and store the information in EHR database 114. In an alternative embodiment, the information about the multiple patients may already be stored in EHR database 114 from previous active patient risk predictions. In yet another alternative embodiment, the information about multiple patients may be stored by a hospital or healthcare network and ARP program 112 can access this information via network 102.

ARP program 112 creates a risk prediction model (step S210). ARP program 112, using the EHR data, learns a prediction model, which will be later used to estimate the risk that a patient will suffer from a particular disease. The reconstruction error may be represented as Equation (1). In an embodiment, the reconstruction weight (patient similarity matrix) S is solved as a constrained least square problem. In an alternative embodiment, it can be solved as a linear system of equations. In yet another embodiment, it can be solved as a quadratic program (QP).

$$Q(S) = \sum_{i=1}^{n} // p_i = \sum_{p_j \in \mathcal{G}_{p_i}} S_{ij} p_j I^2 \qquad (1)$$

An advantage of using a QP formulation is that additional constraints (such as non-negativity) can be added in, and thereby makes the formulation more flexible. $I^i$ denotes the local covariance matrix of patient $p_i$ (the term "local" refers to the fact that the patient is used as the mean in the calculation of covariance). The definition of can be expressed as $I^i = (1p_i - \mathcal{G}_{p_i})(1p_i - \mathcal{G}_{p_i})^T$, where 1 denotes a column vector consisting of ones. It should be noted that the superscript "T" denotes "transpose", a basic matrix operation. Using the local covariance matrix, the reconstruction error problem can be reformulated to a series of small QP problems (one for each patient), since each row of S is independent of every other. Formally, a row vector $S_i$. (the weights used to reconstruct patient $p_i$ using its neighbors) in the similarity matrix S can be solved as a QP problem represented as Equation (2). It should be noted that the term "s.t." is short for "subject to".

$$\min_{S_{i\cdot}} S_{i\cdot} \mathcal{L}^i S_{i\cdot}^T \qquad (2)$$
$$\text{s.t.} \quad S_{i\cdot} 1 = 1;$$
$$S_{ij} \geq 0, \forall j \in \{1, 2, \ldots, n\}$$

The unconstrained version of patient similarity can be learned using Equation (2). The relative similarities (neighborhood ordering) are encoded into the formulation, such that the feedback from humans can be incorporated to the similarity matrix of patients. The QP formulation of the reconstruction error represented in Equation (2) allows ARP program 112 to encode the neighborhood orderings as a set of linear constraints to the patient similarity matrix S.

A simplified example to show the enforcement of relative similarities on a group of just three patients (the minimum number of patients for a relative patient similarity) can be shown where given that a patient $p_i$ has two neighboring (similar) patients $p_a$ and $p_b$, and patient $p_a$ is more similar to patient $p_i$ than $p_b$. It is then claimed that the weight of $p_a$ used to reconstruct $p_i$ should be greater than the weight of $p_b$, i.e., $S_{ia} \geq S_{ib}$. This relative similarity can be encoded to the QP formulation using the linear constraint as represented in Equation (3). In Equation (3) $e^a$ is a single-entry column vector with the a-th entry being one and all the other entries being zeros. With the transivity of inequality, a complete ordering on a group of neighboring patients can be enforced using a set of concatenating constraints. In an alternative example, if it is required that patient $p_a$, $p_b$, and $p_c$ are decreasingly similar to patient $p_i$, i.e., in terms of patient similarity they have $S_{ia} \geq S_{ib} \geq S_{ic}$. then this ordering can be enforced using two concatenating constraints, i.e., $S_i \cdot (e^a - e^b) \geq 0$ and $S_i \cdot (e^b - e^c) \geq 0$.

$$\min_{S_i} S_i \cdot \mathcal{L}^i S_i^T \quad (3)$$
$$\text{s.t. } S_i \cdot (e^a - e^b) \geq 0;$$
$$S_i \cdot 1 = 1;$$
$$S_{ij} \geq 0, \forall j \in \{1, 2, \ldots, n\}$$

ARP program 112 identifies a neighboring group to the subject patient (step S215). With the QP formulation shown in Equation (3), the patient similarity matrix S can be learned under the guidance of the relative similarities provided by medical experts. Next, we must address the informative patient neighborhoods, which will be prompted to human experts as queries. ARP program 112 aims to choose the patient neighborhood which if queried (sorted by human experts) will have the most significant impact in terms of better propagating the risk of diseases on the patient graph. Since each neighboring set of patients naturally forms a subset of the n patients, the counter set cover is used to estimate the importance of a patient neighborhood.

A cover set problem consists of two parts: (i) a universe which in our case is a patient set $\mathcal{P}$ containing all the n patients; and (ii) a set of subsets of $\mathcal{P}$ which in our case is the n patient neighbor sets that correspond to the n patients, i.e., $\mathcal{G} = \{\mathcal{G}_{p1}, \mathcal{G}_{p2}, \ldots, \mathcal{G}_{pn}\}$. A subset $\mathcal{G}s$ of $\mathcal{G}s(\mathcal{G}s \subset \mathcal{G})$ is a cover of the universe $\mathcal{P}$ if every patient in $\mathcal{P}$ appears at least once in $\mathcal{G}s$. In other words, the union of the subsets in $\mathcal{G}s$ is the universe, i.e., $\cup \mathcal{G}s_i = \mathcal{P}$. A cover $\mathcal{G}s$ that has minimum (possibly weighted) cardinality is called a minimum set cover. The set cover problem, which aims to identify such a minimum cover, is represented as Equation (4), where $c_i$ is the indicator of the subset $\mathcal{G}_{pj}$ (the neighborhood of patient $p_j$), which is set to 1 if the neighborhood $\mathcal{G}_{pj}$ is part of the minimum set cover, and 0 otherwise. $\mathcal{B}_{ij}$ indicates whether the patient $p_i$ exists in the neighborhood $\mathcal{G}_{pj}$ (the neighborhood of patient $p_j$), i.e., $\mathcal{B}_{ij}=1$ if $p_i \in \mathcal{G}_{pj}$ and $\mathcal{B}_{ij}=0$ otherwise. The first constraint in Equation (4) is to guarantee that every patient in $\mathcal{P}$ is covered at least once in the solution, and the second constraint is to enforce the set cover indicator to be binary, i.e., $c_i$ is either 0 or 1.

$$\min \sum_{i=1}^{n} C_i \quad (4)$$
$$\text{s.t. } \sum_{j=1}^{n} \mathcal{B}_{ij} C_j \geq 1, \quad \forall p_i \in \mathcal{P}$$
$$C_i \in \{0, 1\}$$

The set cover is a well studied NP-hard (Non-deterministic Polynomial-time hard) problem. The following greedy approximation algorithm is used to solve the set cover problem: in each step, choose the subset $\mathcal{G}_{pi}$ that contains the most uncovered patients and repeat this process until all patients are covered. This simple greedy approach finds a set cover with at most $c^* \log_s^n$ sets, where an optimal solution contains $c^*$ sets. With random initializations this method produces multiple close to minimum set covers. This allows the number of solutions that each patient neighborhood $\mathcal{G}_{pi}$ participates in to be counted and make the estimation of each neighborhood's significance easier. $Q(\mathcal{G}_{pi})$ denotes the significance of patient $P_i$'s neighborhood to maintain the graph structure. The weighted counting set cover problem is represented as Equation (5), where $z_j$ denotes a close to minimum set cover solution, and $\mathcal{Z}$ denotes the collection of the multiple close to minimum set covers. $\gamma(\mathcal{G}_{pi}, z_j)$ indicates whether the neighborhood $\mathcal{G}_{pi}$ is part of the (close to minimum) set cover $z_j$. Formally, $\gamma(\mathcal{G}_{pi}, z_j)=1$ if $\mathcal{G}_{pi} \in z_j$, and $\gamma(\mathcal{G}_{pi}, z_j)=0$ otherwise. $w(\mathcal{G}_{pi})$ is the counting weight of patient neighborhood $\mathcal{G}_{pi}$, which also can be viewed as defining the querying preference of patient neighborhoods.

$$Q(\mathcal{G}_{p_i}) = \sum_{z_j \in Z} \gamma(\mathcal{G}_{p_i}, z_j) w(\mathcal{G}_{p_i}) \quad (5)$$

In an embodiment, a uniform weighting scheme, represented as Equation (6) is used. This is a baseline weighting scheme that assigns a uniform weight to all patient neighborhoods. The underlying assumption of this weighing scheme is that all patient neighborhoods are equally important in the counting, and therefore, from the weighting perspective they are equally likely to be selected.

$$w(\mathcal{G}_{pi})=1, \forall \mathcal{G}_{pi} \in \mathcal{G} \quad (6)$$

In an alternative embodiment, a connectivity weighting scheme, represented as Equation (7) is used. The counting weight of a neighborhood $\mathcal{G}_{pi}$ is proportional to the frequency that the members of $\mathcal{G}_{pi}$ is are used to reconstruct others. This weighting scheme is node (patient) connectivity based, which assigns higher weights to the patient neighborhoods that are located in the "dense" area of the patient similarity matrix S. That is where the learning algorithm is more likely to be confused. This implies that the weighting scheme prefers to query the patient neighborhoods that are highly connect to others, including both within and outside the neighborhood, since they are more influential in maintaining the key structure of the patient graph.

$$w(\mathcal{G}_{p_i}) = \sum_{j=1}^{n} S_{ji} \quad (7)$$

ARP program 112 receives an experts ordering of the determined neighboring group and the patient (step S220). Once an informative patient neighborhood is identified by the counting set cover strategy (step S215), a medical expert will be asked to sort the neighbors in descending order with respect to the similarity to the original patient that they are neighbors of. The relative similarities obtained from human experts will be later incorporated to the learning of the patient similarity matrix S, as determined in step S210, which in turn improvise the prediction accuracy of patient risks.

ARP program 112 updates the risk prediction model (step S225). As discussed previously, Equation (2) is used to incorporate the feedback of the ordering of neighboring groups and the original patient, from step S220, into the risk prediction model created in step S210. The learning of similarity is constrained by the relative ordering (feedback from humans), which leads to the type of similarity that humans prefer. The QP formulation of the reconstruction error in Equation (2) allows for the encoding of the neighborhood orderings as a set of linear constraints to the patient similarity matrix S. With the QP formulation shown in Equation (3), the risk prediction model can be updated with the inclusion of the similarities provided by medical experts.

ARP program 112 determines if the risk prediction model is accurate (decision block S230). In an embodiment, the risk prediction model will be determined to be accurate when updating the risk prediction model (step S225), based on the medical experts ordering of neighboring groups and the original patient (step S220), does not change the risk prediction model. In an alternative embodiment, the risk prediction model will be determined to be accurate when stopping criterion is satisfied. For example, after three iterations of determining neighboring groups and medical experts ordering the neighboring groups and the original patient. Alternatively, when the patient similarity converges in the constrained (by the human feedback) similarity learning process, the risk prediction model can be determined to be accurate, since patient similarity is the (underlying) key of the risk prediction model.

If the risk prediction model is not accurate (decision block 5230, false branch), then ARP program 112 proceeds to identify a new neighboring group (step S215). If the risk prediction model is accurate (decision block 5230, true branch), then ARP program 112 proceeds to estimate patient risk (step S235).

ARP program estimates patient risk (step S235). After the active learning of patient similarity matrix S, patient risk prediction can be performed using graph diffusion methods. In particular, the givens risks of diseases are propagated on the patient graph using the similarity matrix S. Each row of the patient similarity matrix S sums to one, thereby S can be readily used as the transition matrix and perform a random walk on the graph to infer patients risks. In each risk propagation iteration, the state (i.e. the risks of the diseases), of each patient is partially (with a rate of λ) adjusted by risk values that flow on the graph, but still preserve a portion (with a rate of 1–λ) of the given true risks. $\mathcal{R}$ denotes the predicted patient risk and $\mathcal{B}$ denotes the given true risk, the state (risk) of patients at time t+1 can be inferred from the previous state of patients at time t, represented by Equation (8).

$$\mathcal{R}^{t+1} = \lambda S \mathcal{R}^t + (1-\lambda) \mathcal{B} \qquad (8)$$

$\mathcal{R}^\infty$ denotes the patient state (risk) after infinite random walk steps, as represented by Equation (9), and the state of patients eventually converges to a steady-state probability, where I denotes the identity matrix. The value of (1–λ) can be interpreted as the probability of the restart (jump back to the initial state) in a random walk. The restart is a necessary step in the risk propagation process, otherwise the problem would reduce to a global solution, which is equivalent to the result of PageRank. PageRank is a ranking method that ranks nodes (based on their "popularity") on a graph, for example, search engines may use PageRank type method to rank webpages. (1–λ) can also be viewed as the constant to penalize the changes to the initial risk. I the given risk $\mathcal{B}$ is relatively more complete ($\mathcal{B}$ is a dense matrix), a smaller value should be set for λ. Alternatively, the value of λ should be larger if the given risk $\mathcal{B}$ is relatively less complete ($\mathcal{B}$ is a sparse matrix) or contains a considerable amount of noise.

$$\mathcal{R}^\infty = (1-\lambda)(1-\lambda S)^{-1} B \qquad (9)$$

In an example, the final goal is to predict if a person is mentally healthy based on his or her structural MRI scan. Typically, this is a difficult problem to solve since there is not enough training data to obtain an accurate prediction model. Such types of training data is hard and expensive to obtain since it is difficult to track the health record of patients (patients may move to another place, may go to another hospital, or may not want to share his or her medical records). Additionally, it requires a doctor to determine if a patient is mentally healthy or not, and the labor expense of doctors can be quite high. Typical questions can be very challenging to answer. For example, will this patient suffer from Alzheimer's later in his or her life? This is a difficult question even for a doctor. Alternatively, are Patient 1 and Patient 2 similar or not? This question cannot be answered without a medical background.

Using the above described method, it is not necessary to determine if a patient is healthy or not, rather the relative similarity between patients is compared, which is much easier and can be done even without a medical background. For example, is Patient 2 or Patient 3 more similar to Patient 1? This is an easy question, since people without medical background can answer this question by simply comparing three images in the case of a structural MRI scan. In this way, the above described method significantly reduces the cost of the collection of medical training data, which in turn makes the risk prediction model possible or more accurate.

Figure 3:
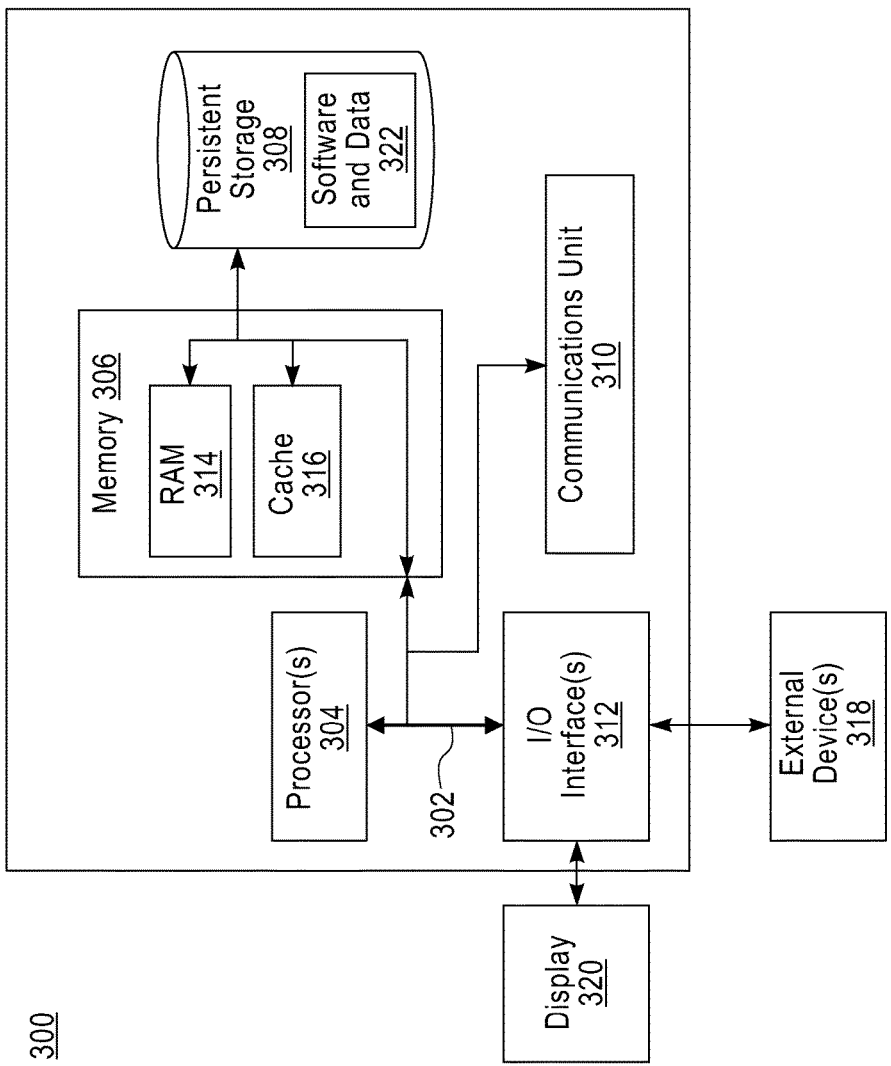
FIG. 3 depicts a block diagram of components of a computing system representative of the computer of FIG. 1, in accordance with an embodiment of the present invention.

FIG. 3 depicts a block diagram of components of computer 300, in accordance with an illustrative embodiment of the present invention. In an embodiment, computer 300 is representative of computer 110. It should be appreciated that FIG. 3 provides only an illustration of one implementation and does not imply any limitations with regard to the environments in which different embodiments may be implemented. Many modifications to the depicted environment may be made.

Computer 300 includes communications fabric 302, which provides communications between computer processor(s) 304, memory 306, persistent storage 308, communications unit 310, and input/output (I/O) interface(s) 312. Communications fabric 302 can be implemented with any architecture designed for passing data and/or control information between processors (such as microprocessors, communications and network processors, etc.), system memory, peripheral devices, and any other hardware components within a system. For example, communications fabric 302 can be implemented with one or more buses.

Memory 306 and persistent storage 308 are computer readable storage media. In this embodiment, memory 306 includes random access memory (RAM) 314 and cache memory 316. In general, memory 306 can include any suitable volatile or non-volatile computer readable storage media. Software and data 322 are stored in persistent storage 308 for access and/or execution by processors 304 via one or more memories of memory 306. With respect to computer 110, software and data 322 includes ARP program 112 and EHR database 114.

In this embodiment, persistent storage 308 includes a magnetic hard disk drive. Alternatively, or in addition to a magnetic hard disk drive, persistent storage 308 can include a solid state hard drive, a semiconductor storage device, read-only memory (ROM), erasable programmable read-only memory (EPROM), flash memory, or any other computer readable storage media that is capable of storing program instructions or digital information.

The media used by persistent storage 308 may also be removable. For example, a removable hard drive may be used for persistent storage 308. Other examples include optical and magnetic disks, thumb drives, and smart cards that are inserted into a drive for transfer onto another computer readable storage medium that is also part of persistent storage 308.

Communications unit 310, in these examples, provides for communications with other data processing systems or devices. In these examples, communications unit 310 may include one or more network interface cards. Communications unit 310 may provide communications through the use of either or both physical and wireless communications links. Software and data 322 may be downloaded to persistent storage 308 through communications unit 310.

I/O interface(s) 312 allows for input and output of data with other devices that may be connected to computer 300. For example, I/O interface 312 may provide a connection to external devices 318 such as a keyboard, keypad, a touch screen, and/or some other suitable input device. External devices 318 can also include portable computer readable storage media such as, for example, thumb drives, portable optical or magnetic disks, and memory cards. Software and data used to practice embodiments of the present invention, e.g., ARP program 112, can be stored on such portable computer readable storage media and can be loaded onto persistent storage 308 via I/O interface(s) 312. I/O interface(s) 312 also can connect to a display 320.

Display 320 provides a mechanism to display data to a user and may be, for example, a computer monitor. Display 320 can also function as a touch screen, such as a display of a tablet computer.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A method for updating a patient risk prediction model, the method comprising:
   receiving electronic health records of a plurality of patients;
   creating, by one or more computer processors, a risk prediction model for a disease based on the electronic health records of the plurality of patients;
   receiving, by one or more computer processors, an electronic health record of an original patient;
   identifying, by one or more computer processors, a neighboring group of patients of the plurality of patients, wherein the neighboring group of patients is two or more patients similar to the original patient;
   generating, by one or more computer processors, a question as to a relative ordering of the two or more patients of the neighboring group of patients with respect to the original patient;
   receiving an answer to the question as to the relative ordering of the two or more patients of the neighboring group of patients, wherein the ordering of the two or more patients of the neighboring group of patients is based upon how similar each patient of the two or more patients is to the original patient; and
   updating, by one or more computer processors, the risk prediction model based on the answer to the question as to the relative ordering of the two or more patients of the neighboring group of patients.

2. The method of claim 1, further comprising:
   estimating, by one or more computer processors, the risk that the original patient will suffer from the disease based upon the updated risk prediction model.

3. The method of claim 1, wherein the ordering of the patients of the neighboring group of patients is a complete ordering including all patients of the neighboring group of patients or a partial ordering including at least one of the patients of the neighboring group of patients.

4. The method of claim 1, wherein the risk prediction model for a disease based on the plurality of patients is selected from a group consisting of: constrained least square problem, a linear system of equations, or a quadratic program.

5. The method of claim 1, wherein the risk prediction model is updated until a patient similarity converges in a constrained similarity process.

6. The method of claim 1, wherein the risk prediction model is updated more than one time.

7. The method of claim 1, wherein the electronic health record includes one or more of the following: demographics; medical history; medication and allergies; immunization status; laboratory test results; radiology images; vital signs; and personal statistics.

8. A computer program product for updating a patient risk prediction model, the computer program product comprising:
   one or more computer readable storage media and program instructions stored on the one or more computer readable storage media, the program instructions comprising:
      program instructions to receive electronic health records of a plurality of patients;
      program instructions to create a risk prediction model for a disease based on the electronic health records of the plurality of patients;
      program instructions to receive an electronic health record of an original patient;
      program instructions to identify a neighboring group of patients of the plurality of patients, wherein the neighboring group of patients is two or more patients similar to the original patient;
      program instructions to generate a question as to a relative ordering of the two or more patients of the neighboring group of patients with respect to the original patient;
      program instructions to receive an answer to the question as to the relative ordering of the two or more patients of the neighboring group of patients, wherein the ordering of the two or more patients of the neighboring group of patients is based upon how similar each patient of the two or more patients is to the original patient; and
      program instructions to update the risk prediction model based on the answer to the question as to the relative ordering of the two or more patients of the neighboring group of patients.

9. The computer program product of claim 8, further comprising program instructions, stored on the one or more computer readable storage media, to:
   estimate the risk that the original patient will suffer from the disease based upon the updated risk prediction model.

10. The computer program product of claim 8, wherein the ordering of the patients of the neighboring group of patients is a complete ordering including all patients of the neighboring group of patients or a partial ordering including at least one of the patients of the neighboring group of patients.

11. The computer program product of claim 8, wherein the risk prediction model for a disease based on the plurality of patients is selected from a group consisting of: constrained least square problem, a linear system of equations, or a quadratic program.

12. The computer program product of claim 8, wherein the risk prediction is updated until a patient similarity converges in a constrained similarity process.

13. The computer program product of claim 8, wherein the risk prediction model is updated more than one time.

14. The computer program product of claim 8, wherein the electronic health record includes one or more of the following: demographics; medical history; medication and allergies; immunization status; laboratory test results; radiology images; vital signs; and personal statistics.

15. A computer system for updating a patient risk prediction model, the computer system comprising:
   one or more computer processors;
   one or more computer readable storage media; and
   program instructions stored on the computer readable storage media for execution by at least one of the one or more processors, the program instructions comprising:
   program instructions to receive electronic health records of a plurality of patients;
   program instructions to create a risk prediction model for a disease based on the electronic health records of the plurality of patients;
   program instructions to receive an electronic health record of an original patient;
   program instructions to identify a neighboring group of patients of the plurality of patients, wherein the neighboring group of patients is two or more patients similar to the original patient;
   program instructions to generate a question as to a relative ordering of the two or more patients of the neighboring group of patients with respect to the original patient;
   program instructions to receive an answer to the question as to the relative ordering of the two or more patients of the neighboring group of patients, wherein the ordering of the two or more patients of the neighboring group of patients is based upon how similar each patient of the two or more patients is to the original patient; and
   program instructions to update the risk prediction model based on the answer to the question as to the relative ordering of the two or more patients of the neighboring group of patients.

16. A computer system of claim 15, further comprising program instructions, stored on the one or more computer readable storage media for execution by the at least one of the one or more computer processors, to:
   estimate the risk that the original patient will suffer from the disease based upon the updated risk prediction model.

17. A computer system of claim 15, wherein the ordering of the patients of the neighboring group of patients is a complete ordering including all patients of the neighboring group of patients or a partial ordering including at least one of the patients of the neighboring group of patients.

18. A computer system of claim 15, wherein the risk prediction model for a disease based on the plurality of patients is selected from a group consisting of: constrained least square problem, a linear system of equations, or a quadratic program.

19. A computer system of claim 15, wherein the risk prediction model is updated more than one time.

20. A computer system of claim 15, wherein the electronic health record includes one or more of the following: demographics; medical history; medication and allergies; immunization status; laboratory test results; radiology images; vital signs; and personal statistics.

* * * * *